(12) United States Patent
Aslan et al.

(10) Patent No.: US 8,142,773 B2
(45) Date of Patent: Mar. 27, 2012

(54) METHODS OF IMPLANTING MESENCHYMAL STEM CELLS FOR TISSUE REPAIR AND FORMATION

(75) Inventors: Hadi Aslan, Magar (IL); Dan Gazit, Maccabim (IL); Zulma Gazit, Maccabim (IL)

(73) Assignee: Yissum Research Development Company of the hebrew University of Jerusalem, Jerusalem (IL)

( * ) Notice: Subject to any disclaimer, the term of this patent is extended or adjusted under 35 U.S.C. 154(b) by 90 days.

(21) Appl. No.: 12/007,954

(22) Filed: Jan. 17, 2008

(65) Prior Publication Data

US 2008/0112936 A1 May 15, 2008

Related U.S. Application Data

(62) Division of application No. 10/520,271, filed as application No. PCT/IL03/00587 on Jul. 15, 2003, now abandoned.

(60) Provisional application No. 60/396,010, filed on Jul. 16, 2002.

(51) Int. Cl.
*A61K 48/00* (2006.01)
(52) U.S. Cl. ............... 424/93.7; 424/93.1; 424/93.21
(58) Field of Classification Search .......... 424/93.7, 424/93.1, 93.21
See application file for complete search history.

(56) References Cited

U.S. PATENT DOCUMENTS

| 5,486,359 | A | 1/1996 | Caplan et al. | |
|---|---|---|---|---|
| 5,965,436 | A | 10/1999 | Thiede et al. | |
| 6,043,066 | A | 3/2000 | Mangano et al. | |
| 6,387,367 | B1 | 5/2002 | Davis-Sproul et al. | |
| 2002/0142457 | A1* | 10/2002 | Umezawa et al. | 435/366 |
| 2002/0169122 | A1* | 11/2002 | Majumdar et al. | 514/12 |
| 2005/0249731 | A1 | 11/2005 | Aslan et al. | |

FOREIGN PATENT DOCUMENTS

| WO | WO 93/00050 | 1/1993 |
|---|---|---|
| WO | WO 01/11011 | 2/2001 |
| WO | WO 2004/007697 | 1/2004 |

OTHER PUBLICATIONS

Horwitz et al. (Nov. 2000) Blood 96 (11 Part 1): p. 800a, abstract.*
Aslan et al. "Osteogenic Differentiation of Noncultured Immunoisolated Bone Marrow-Derived CD105+ Cells", Stem Cells, 24(7): 1728-1737, 2006.
Caplan et al. "Mesenchymal Stem Cells: Building Block for Molecular Medicine in the 21st Century", Trends in Molecular Medicine, 7(6): 259-264, 2001.
Clarke et al. "Mesenchymal Cell Precursors From Human Bone Marrow Have a Phenotype That Is Distinct From Cultured Mesenchymal Cells and Are Exclusively Present in a Small Subset of CD451° SH2+ Cells", Blood, 98(11 Part 1): 85a, 2001. Abstract # 355.
Devine et al. "Mesenchymal Stem Cells Are Capable of Homing to the Bone Marrow of Non-Human Primates Following Systemic Infusion", Experimental Hematology, 29(2): 244-255, 2001.
Fridenshtein "Stromal Bone Marrow Cells and the Hematopoietic Microenvironment", Arkh Patol, 44(10): 3-11, 1982. Abstract.
Gronthos et al. "The Growth Factor Requirements of STRO-1-Human Bone Marrow Stromal Precursors Serum-Deprived Conditions In Vitro", Blood, 85(4): 992-940, 1995.
Haynesworth et al. "Characterization of Cells With Osteogenic Potential From Human Marrow", Bone, 13: 81-88, 1992.
Horowitz et al. "Transplantability and Therapeutic Effects of Bone Marrow-Derived Mesenchymal Cells in Childern With Osteogenesis Imperfecta", Nature Medicine, 5(3): 309-313, 1999.
Kadiyala et al. "Culture Expanded Canine Mesenchymal Stem Cells Possess Osteochondrogenic Potential In Vivo and In Vitro", Cell Transplantation, 6(2): 125-134, 1997.
Keunmyoung et al. "Human Mesenchymal Stem Cells MaintainTransgene Expression During Expansionand Differentiation", Molecular Therapy, 3(6): 857-866, 2001.
Krebsbach et al. "Repair of Craniotomy Defects Using Bone Marrow Stromal Cells", Transplantation, 66(10): 1272-1278, 1998.
Liechty et al. "Human Mesenchymal Stem Cells Engraft and Demonstrate Sitespecific Differentiation After In Utero Transplantation in Sheep", Nature Medicine, 6(11): 1282-1286, 2000.
Mackay et al. "Chondrogenic Differentiation of Cultured Human Mesenchymal Stem Cells From Marrow", Tissue Engineering, 4(4): 415-428, 1998.
Majumdar et al. "Cutting Edge Communication—Human Marrow-Derived Mesenchymal Stem Cells (MSCs) Express Hematopoietic Cytokines and Support Long-Term Hematopoiesis When Differentiated Toward Stromal and Osteogenic Lineages", Journal of Hematotherapy & Stem Cell Research, 9: 841-848, 200.
Majumdar et al. Isolation, Characterization, and Chondrogenic Potential of Human Bone Marrow-Derived Multipotential Stromal Cells, Journal of Cellular Physiology, 185: 98-106, 2000.
Pelled et al. "Mesenchymal Stem Cells for Bone Gene Therapy and Tissue Engineering", Current Pharmaceutical Design, 8: 1917-1928, 2002.
Pittenger et al. "Human Mesenchymal Stem Cells Can Be Directed Into Chondrocytes, Adipocytes and Osteocytes", Molecular Biology of the Cell, 305a: 1772, 1996. Abstract.
Pittenger etal. "Multilineage Potential of Adult Human Mesenchymal Stem Cells", Science, 284(5411): 143-147, 1999.
Quirici et al. "Isolation of Bone Marrow Mesenchymal Stem Cells by Anti-Nerve Growth Factor Receptor Antibodies", Experimental Hematology, 30(7): 783-791, 2000.
Toma et al. "Human Mesenchymal Stem Cells Differentiate to a Cardiomyocyte Phenotype in the Adult Murine Heart", Circulation, 105: 93-98, 2002.
Turgeman et al. "Cell-Mediated Gene Therapy for Bone Formation and Regeneration", Current Opinion in Molecular Therapeutics, 4(4): 390-394, 2002.
Turgeman et al. "Engineered Human Mesenchymal Stem Cells: A Novel Platform for Skeletal Cell Mediated Gene Therapy", The Journal of Gene Medicine, 3: 240-251, 2001.

(Continued)

*Primary Examiner* — Anne Marie S Wehbe

(57) ABSTRACT

The invention relates to methods of isolating and implanting mesenchymal stem cells for tissue repair or formation, without prior culture expansion of the mesenchymal stem cells. In particular, the invention relates to methods of isolating mesenchymal stem cells from bone marrow, for repairing or inducing formation of bone, without prior culture expansion of the mesenchymal stem cells. The invention further relates to an isolated, non-culturally expanded human adult mesenchymal stem cell population.

22 Claims, 8 Drawing Sheets

OTHER PUBLICATIONS

Yoo et al. "The Cohondrogenic Potential of Human Bone-Marrow-Derived Mesenchymal Progenitor Cells", Journal of Bone and Joint Surgery, 80(12): 1745-1757, 1998.

Young et al. "Use of Mesenchymal Stem Cells in a Collagen Matrix for Achilles Tendon Repair", Journal of the Orthopaedic Research, 16: 406-413, 1998.

Official Action Dated Oct. 17, 2007 From the US Patent and Trademark Office Re.: U.S. Appl. No. 10/520,271.

Communication Pursuant to Article 94(3) EPC Dated Feb. 25, 2008 From the European Patent Office Re.: Application No. 03764110.7.

Horwitz et al. "Isolated Allogeneic Bone Marrow-Derived Mesenchymal Cells Engraft and Stimulate Growth in Children With Osteogenesis Imperfecta: Implications for Cell Therapy of Bone", Proc. Natl. Acad. Sci. USA, PNAS, 99(13): 8932-8937, Jun. 25, 2002.

* cited by examiner

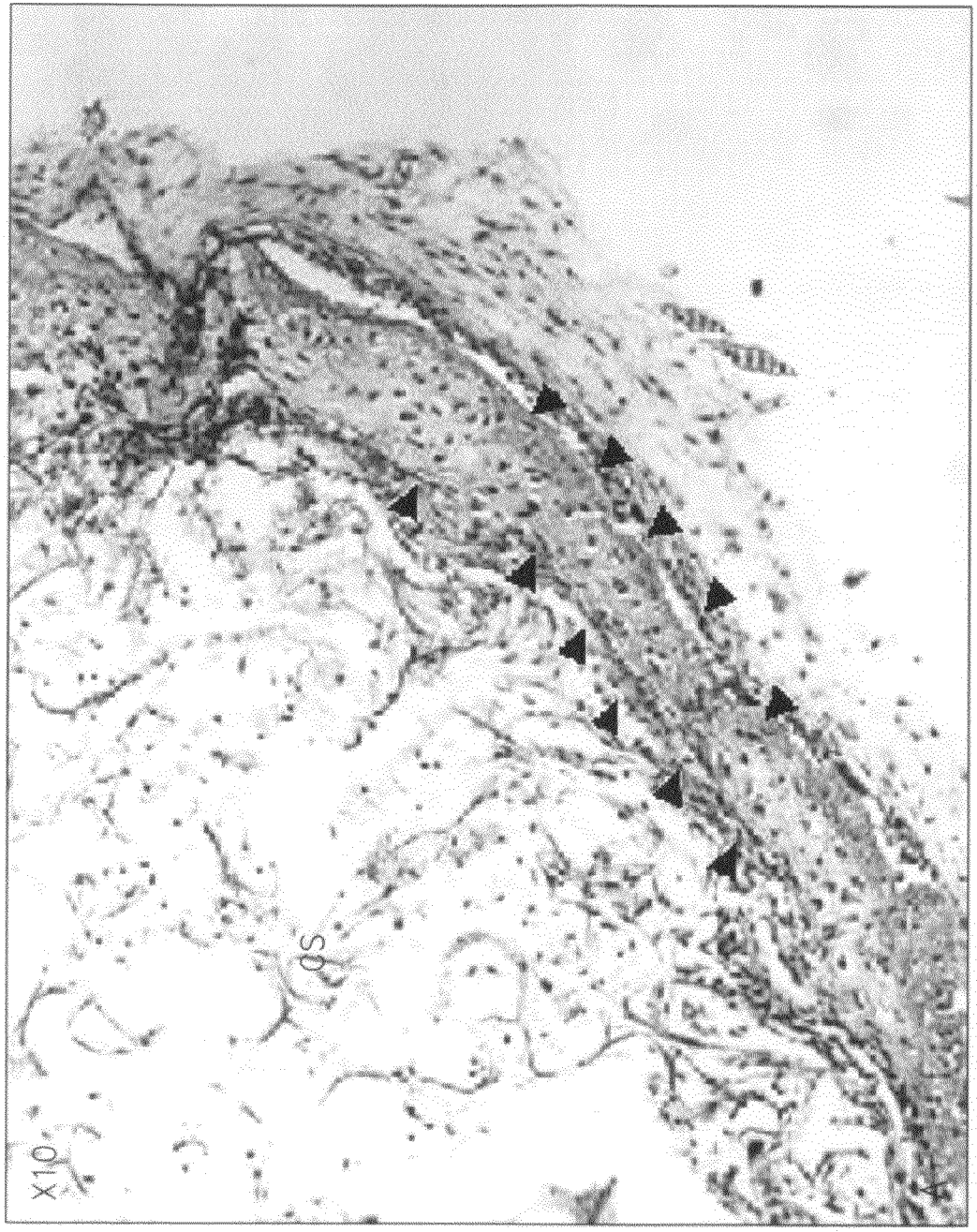

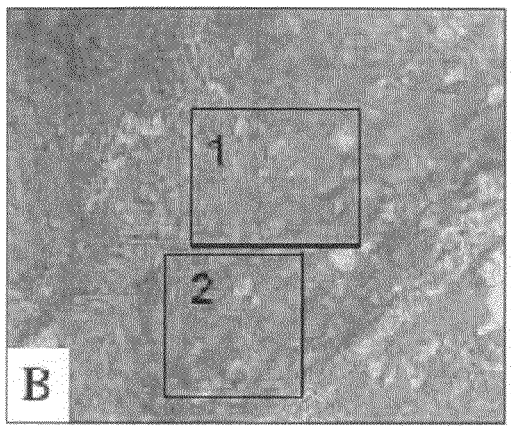
FIG.5B
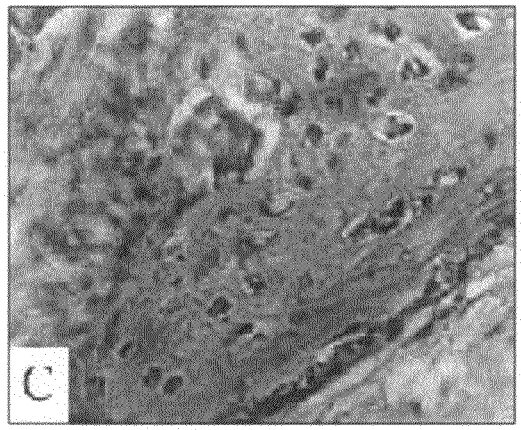
FIG.5C
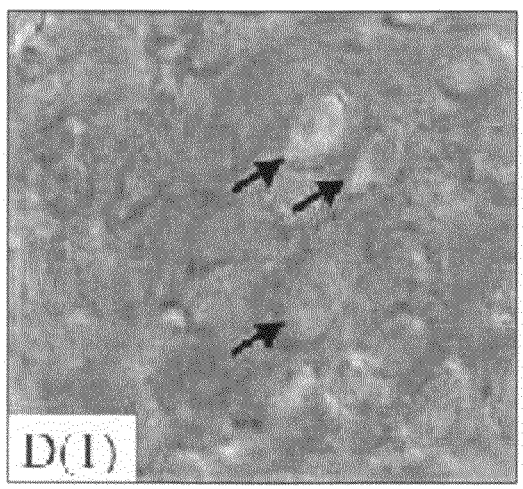
FIG.5D(1)
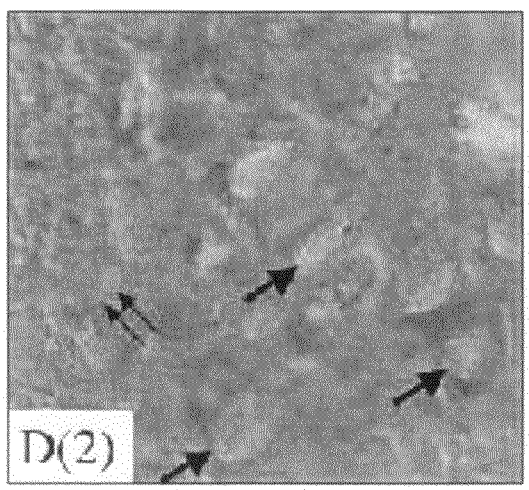
FIG.5D(2)

METHODS OF IMPLANTING MESENCHYMAL STEM CELLS FOR TISSUE REPAIR AND FORMATION

RELATED PATENT APPLICATION

This application is a Divisional of U.S. patent application Ser. No. 10/520,271 filed on Jan. 14, 2005, which is a National Phase Application of PCT/IL2003/000587 having International Filing Date of 15 Jul. 2003, which claims the benefit of U.S. Provisional Patent Application No. 60/396,010 filed 16 Jul. 2002.

BACKGROUND OF THE INVENTION

Mesenchymal stem cells (MSCs) are considered one of the most promising tools for cell and cell-mediated gene therapy in skeletal repair. MSCs were shown to have the potential to differentiate into several lineages including bone (Haynesworth et al., 1992), cartilage (Mackay et al., 1998, Yoo et al., 1998), fat (Pittenger et al., 1996), tendon (Young et al., 1998), muscle, and stroma (Reviewed by Caplan et al, 2001). The main source known of MSCs in adult humans is the bone marrow compartment that contains several cell types including cells of the hematopoietic lineage, endothelial cells, and mesenchymal stem cells, which are part of the marrow stromal system (Pittenger et al, 1999).

Several protocols were recently established in order to enable regeneration and filling of large bone defects, utilizing human MSCs expanded in culture as both the cells differentiating into osteogenic cells, and as the vehicles delivering the therapeutic gene product such as BMP-2 (Turgeman et al., 2001). It was recently shown that in combination with BMP-2, hMSCs are able to heal full-thickness non-union bone defects (Turgeman et al., 2001), and in recent studies it was shown that human MSCs can be transduced by retroviral vectors and maintain stable expression of the therapeutic gene after in vivo transplantation (Lee et al., 2001). Within these studies, the MSCs were isolated from the bone marrow, expanded in culture, in some cases genetically engineered, and transplanted in-vivo. The culture expansion stage is extremely costly, time consuming, and in many cases, the cells may lose their multipotentiality and fail to achieve the desired goal. In contrast, very few studies described the use of non-cultured freshly isolated human MSCs. Horwitz et al., (1999) showed that human MSCs present in unprocessed bone marrow allografts engraft and may provide stem cell reservoir for osteoblast differentiation and renewal. The isolation of hMSCs-enriched population requires efficient and reproductive isolation method. Few methods were described for the isolation of MSCs, including enhancement of the plastic adherence property of the cells by using selected lots of fetal calf serum (Kadiyala et al., 1997, Pittenger et al., 1999), immunomagnetic isolation based on the presence of the STRO-1 surface molecule (Gronthos and Simmons, 1995). Both methods are very hard to be reproduced by other labs and no studies were done to show the differentiation potential of cells before culture expansion. Majumdar et al. (2000) showed that cells from human BM aspirates were isolated by the anti-CD105 (endoglin) antibodies, differentiated to chondrogenic cells after culture expansion, and showed immunophenotype distinctive to MSCs, suggesting that these CD105+cells contain the osteogenic MSCs population.

SUMMARY OF THE INVENTION

The invention relates to methods of isolating non-culture expanded mesenchymal stem cells for use in the preparation of medicaments for tissue repair or formation.

A method of obtaining an isolated, non-culture expanded mesenchymal stem cell, comprising the following steps: contacting a human cell population with an antibody that binds to a surface molecule expressed on a mesenchymal stem cell within the human cell population, so as to form a cell-antibody-complex; recovering the mesenchymal stem cell; maintaining the recovered mesenchymal stem cell under conditions preventing significant cellular expansion; thereby obtaining a non-culture expanded mesenchymal stem cell. In another embodiment, the sample comprising a human cell population is contacted with enrichment growth medium so as to obtain a mixed sample prior to forming the cell-antibody-complex, as described hereinabove.

In another embodiment, there is provided a method of use of an isolated, non-culture expanded mesenchymal stem cell for the preparation of a medicament for administration to a subject, wherein the non-culture expanded mesenchymal stem cell is isolated via obtaining a sample comprising a human cell population; contacting the sample with an antibody that binds to a surface molecule expressed on a mesenchymal stem cell so as to form a cell-antibody-complex; recovering the mesenchymal stem cell, thereby obtaining a non-culture expanded mesenchymal stem cell. In another embodiment, the sample comprising a human cell population is contacted with enrichment growth medium so as to obtain a mixed sample prior to forming the cell-antibody-complex, as described hereinabove.

In another embodiment, there is provided a method of use of an isolated, non-culture expanded mesenchymal stem cell in the preparation of a medicament for stimulating or enhancing tissue repair in a subject, wherein the non-culture expanded mesenchymal stem cell is isolated via obtaining a sample comprising a human cell population; contacting the sample with an antibody that binds to a surface molecule expressed on a mesenchymal stem cell so as to form a cell-antibody-complex; recovering the mesenchymal stem cell, thereby obtaining a non-culture expanded mesenchymal stem cell. In another embodiment, the sample comprising a human cell population is contacted with enrichment growth medium so as to obtain a mixed sample prior to forming the cell-antibody-complex, as described hereinabove.

In another embodiment, there is provided a method of use of an isolated, non-culture expanded mesenchymal stem cell in the preparation of a medicament for stimulating or enhancing tissue formation in a subject, wherein the non-culture expanded mesenchymal stem cell is isolated via obtaining a sample comprising a human cell population; contacting the sample with an antibody that binds to a surface molecule expressed on a mesenchymal stem cell so as to form a cell-antibody-complex; recovering the mesenchymal stem cell, thereby obtaining a non-culture expanded mesenchymal stem cell. In another embodiment, the sample comprising a human cell population is contacted with enrichment growth medium so as to obtain a mixed sample prior to forming the cell-antibody-complex, as described hereinabove.

In another embodiment, there is provided a method of use of an isolated, non-culture expanded mesenchymal stem cell in the preparation of a medicament for maintaining or increasing bone volume, bone quality, or bone strength in a subject, wherein the non-culture expanded mesenchymal stem cell is isolated via obtaining a sample comprising a human cell population; contacting the sample with an antibody that binds to a surface molecule expressed on a mesenchymal stem cell so as to form a cell-antibody-complex; recovering the mesenchymal stem cell, thereby obtaining a non-culture expanded mesenchymal stem cell. In another embodiment, the sample comprising a human cell population is contacted with enrichment growth medium so as to obtain a mixed sample prior to forming the cell-antibody-complex, as described hereinabove.

In another embodiment, this invention provides isolated, non-culture expanded human adult mesenchymal stem cells. In one embodiment, the isolated non-culture expanded human adult mesenchymal stem cells express CD105, CD29 and/or CD44 cell surface antigens.

BRIEF DESCRIPTION OF THE DRAWINGS

FIG. 5 demonstrates engraftment and differentiation of non-cultured hMSCs transplanted at an ectopic site. Non-cultured hMSCs, isolated by the RosetteSep™ were labeled with the fluorescent cell tracer, DiI and implanted with rhBMP. Two weeks following transplantation, implants were harvested, fixed and embedded in OCT. A&B: H&E staining of sections of these implants revealed newly formed cartilage and bone (arrowheads), mainly at the periphery of the implant (original magnification: A: 10×, B: 40×). DiI-labeled cells with chondrocyte (D1, arrow) and osteoblast (D2, doubled arrow) morphology were evident, as well.

DETAILED DESCRIPTION OF THE INVENTION

Figure 1A:
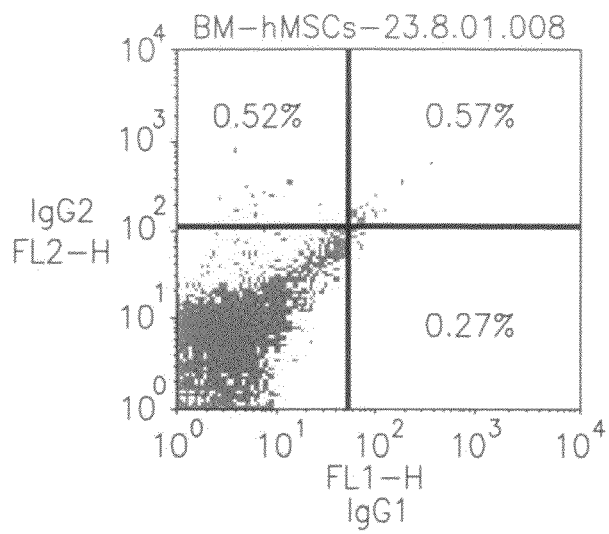
FIG. 1 shows the immunophenotype of bone marrow-derived mononuclear cells. Mononuclear cells (MNCs) were obtained from fresh human BM by separation on a density-gradient. Aliquots of $1 \times 10^6$ cells were stained with the indicated mouse anti-human antibodies. The percent (%) of cells in the quadrants were determined.
Figure 1B:
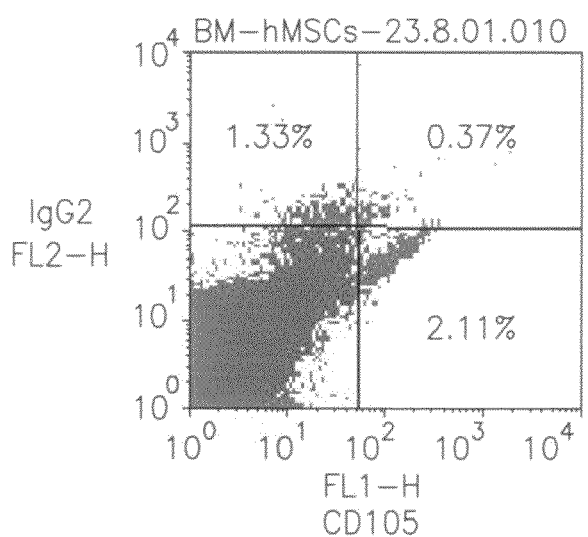

The invention relates to methods of isolating and implanting mesenchymal stem cells for tissue repair or formation, without culture expansion of the mesenchymal stem cells. In one embodiment, the invention relates to methods of isolating mesenchymal stem cells from bone marrow, for repairing or inducing formation of a bone without prior culture expansion of the mesenchymal stem cells.

The tissue is, in one embodiment, a cartilage, or, in another embodiment, a bone or in another embodiment, a ligament tissue. In another embodiment, the tissue is any mammalian tissue in need repair, such as neuronal tissue, striated muscle, cardiac muscle, spleen, liver or kidney, wherein mesenchymal stem cells play a role in such repair.

Mesenchymal Stem Cells (MSCs) are multi-potent cells that can replicate yet maintain their status as undifferentiated cells while possessing the potential to differentiate into specific mesenchymal tissues lineages, including bone, cartilage, fat, tendon, muscle and bone marrow stroma. As used herein, term "MSC" or "mesenchymal stem cells" of the invention comprises, without limitation, embryonic MSC, adult MSC or cord blood stem cells.

This invention provides, in one embodiment, a simple, efficient, and fast platform, for using isolated mesenchymal cells, without culture expansion of the cells prior to their incorporation into a medicament for use in tissue repair or, in another embodiment, for use in tissue formation, or, in another embodiment, for use in bone repair.

The invention provides, in another embodiment, for the use of isolated, non-culture expanded MSC cells in the preparation of a medicament, for administration at any site of interest.

The term "use of isolated, non-culture expanded MSC cells in the preparation of a medicament" refers hereinabove to use of the isolated MSC cells immediately after their isolation or 0-12 hours following their isolation, while avoiding the step of cellular expansion in culture, i.e. cells are kept under conditions significantly preventing their proliferation in culture, prior to their use. By the terms "significantly preventing their proliferation in culture" and "maintaining recovered mesenchymal stem cell under conditions preventing significant cellular expansion", it is to be understood that cellular proliferation is drastically reduced, as a reflection of the culture conditions, the length of time present in culture, or the environmental conditions under which the recovered mesenchymal stem cells are kept.

In one embodiment, cells are cultured for short period of time, which does not exceed 24 hours. In one embodiment, cells are cultured between 1 and 24 hours. In another embodiment, cells are cultured between 1 and 5, or in another embodiment, between 5 and 10, or in another embodiment, between 10 and 15, or in another embodiment, 15 and 20, or in another embodiment, between 20 and 24 hours prior to their use for any method or application of this invention. It is to be understood that any period of time that is less than 24 hours is to be considered as part of this invention, as long as the cells do not undergo expansion while in culture.

In one embodiment, the cells are engineered to express a protein of interest prior to culture. In another embodiment, engineered cells are directly utilized for the methods and/or applications listed herein.

MSCs isolated via the methods disclosed herein, are not culture expanded, hence do not come in contact with plastics or polymers used in long-term cell culture procedures, they are not damaged by stress conditions or infection, which are common occurrences for cells subjected prolonged culture periods.

In one embodiment, MSCs isolated via the methods of this invention, which are to be utilized for the applications listed herein, are utilized immediately following isolation. In another embodiment, cells are transiently cultured (ie less than 24 hours, as discussed hereinabove), prior to their use. In another embodiment, cells may be frozen following isolation, and stored for any length of time that does not radically compromise cell function, pluripotency or viability. Frozen cells may then be thawed and used for methods and applications listed herein.

The term "mesenchymal stem cell" or "MSC" is used interchangeably for cells which are not terminally differentiated, which can divide without limit, to yield cells that are either stem cells, or which, irreversibly differentiate to yield a new type of cell. It is important to note that mesenchymal stem cells and progenitors of the invention can be isolated from different source tissues. In one embodiment, the source tissue is skin, or, in another embodiment, bone marrow, or, in another embodiment, muscle, or, in another embodiment, fat, or, in another embodiment, liver. In addition, any cell type with stem cell properties or demonstrating differentiation plasticity, for example, without limitation, cells from the source of bone marrow, muscle, spleen or any other tissue. Bone marrow cells may be obtained from iliac crest, femora, tibiae, spine, rib or other medullary spaces. Other sources of human mesenchymal stem cells include, without limitation, embryonic yolk sac, placenta, fat, umbilical cord, fetal and adolescent skin, muscle tissue and blood.

In one embodiment, there is provided a method of obtaining an isolated, non-culture expanded mesenchymal stem cell, wherein the cell is obtained by positive selection, via the use of an antibody, which binds to epitope on the cell surface. The method comprises the following steps: obtaining a sample comprising a human cell population; contacting the sample with an antibody that binds to a surface molecule so as to form a cell-antibody-complex; recovering the mesenchymal stem cell; thereby obtaining an isolated, non-culture expanded. The antibody may recognize CD105, as is shown in Example 1 or, may also be other antibodies, which bind to the mesenchymal stem cell surface molecule such as CD44 and CD29. The antibodies may be supported on a column, plastic, array or magnetic bead.

Upon forming an antigen-antibody complex, the antigen-antibody complexes are separated from the other subpopulations which are not bound to the antibody by a column, for example. Where the antibody is supported by a magnetic bead, a magnetic column can be used.

The step of recovering the cells from the antibodies is performed by washes with suitable buffers, known to one skilled in the art. In another embodiment, there is provided a method of obtaining an isolated, non-culture expanded mesenchymal stem cell by negative selection comprising the following steps: obtaining a sample comprising a human cell population; administering to the sample enrichment growth medium so as to obtain a mixed sample; separating the mixed sample so as to obtain a mesenchymal stem cell; recovering the mesenchymal stem cell; thereby obtaining an isolated, non-culture expanded mesenchymal stem cell from a sample. The enrichment growth medium can be, for example without limitation, RosetteSep™ Mesenchymal Enrichment Cocktail (StemCell Technologies BC, Canada). The step of separating the mixed sample so as to obtain a mesenchymal stem cell is known in the art and is performed, for example without being limited, by the use of a centrifuge. In another embodiment the cells can be negative selected by the use of antibodies, which are directed to the surface of other subpopulation, which exist in the sample. For example, as is shown in U.S. Pat. No. 5,965,436, a bone marrow sample may be subjected to negative selection for removal of megakaryocytes from other hematopoietic cells via antibody sorting and mesenchymal cell subpopulations are than obtained. It is to be understood that any method employing mesenchymal stem cell selection, without culture expansion, whether via positive or negative selection, is considered as part of this invention.

In another embodiment, the cell can be separated according to U.S. Pat. No. 6,043,066 by utilizing electric fields to selectively inactivate and render non-viable particular subpopulations of cells in a suspension, while not adversely affecting other desired subpopulations. According to the methods, the cells can be selected on the basis of intrinsic or induced differences in a characteristic electroporation threshold; which can depend, for example, on a difference in cell size and/or critical dielectric membrane breakdown voltage.

The presence of MSCs in isolated cells may be verified by specific cell surface markers which are identified with unique monoclonal antibodies, for example, see U.S. Pat. No. 5,486,359.

Example 1 demonstrated that when cells were positively selected and isolated with CD105 antibodies, as well as by negative selection, the CD105+cells were found to stain positive for the CD105 (endoglin), CD29 (Beta 1 Integrin) and CD44 (Hyaluronate) surface markers. The isolated cells were found to stain negatively for hematopoietic markers CD14 (macrophage marker), and CD45 (leukocyte common antigen). These results demonstrated that cells isolated according to the methods presented herein were MSCs. In addition, as shown assays measuring calcium deposition and ALP activity, in cells cultured in the presence of ascorbate, beta-glycerophosphate, and dexamethasone, demonstrated CD105+ MSC differentiation to osteoblasts, thus, these isolated MSCs express surface antigens characteristic of mesenchymal stem cells alone, can regenerate in culture without differentiating, and can differentiate into specific mesenchymal lineages when either induced in vitro (Example 2) or in vivo, when placed at the site of damaged tissue (Example 3).

Although human MSCs are normally present in bone marrow in minute amounts, which greatly decrease with age (from about 1/10,000 cells in a relatively young patient to as few as 1/2,000,000 in an elderly patient), this invention provides a process for obtaining isolated cells for administration to a subject without prior culture expansion.

New bone formation was evident when non-cultured CD105+ cells were transplanted in nude mice that underwent critical-sized non-healing skull defects (Example 3). These results demonstrated that non-culture expanded bone marrow derived CD105+ cells are osteogenic cells that can be used for bone repair. In addition, as multi-potent cells, non-culture expanded MSCs can be utilized in other application such as cell therapy for tissue repair, hematopietic reconstitution and in any kind of procedure utilized in regenerative medicine.

In another embodiment, there is provided a method of use of an isolated, non-culture expanded mesenchymal stem cell in the preparation of a medicament for administration to a subject, wherein the non-culture expanded mesenchymal stem cell is obtained via the methods described herein.

The medicament is formulated for use topically, systemically, or locally as an injectable and/or transplant and/or device, usually by adding necessary buffers. The cells when suspended in appropriate buffers are referred to compositions/cultures of non-culture expanded cells. When formulated for administration, the non-culture expanded cells used in this invention are, of course, in a pyrogen-free, physiologically acceptable form. Further, the non-culture expanded cells, may be injected in a viscous form for delivery to the site of tissue damage. Topical administration may be suitable for wound healing and tissue repair. In one embodiment, therapeutically useful agents may also optionally be included in the cell composition as described above, or, in other embodiments, may alternatively or additionally, be administered simultaneously or sequentially with the composition in the methods of the invention.

In another embodiment, the compositions of the present invention may be used in conjunction with presently available treatments for tendon/ligament injuries, such as suture (e.g., vicryl sutures or surgical gut sutures, Ethicon Inc., Somerville, N.J.) or tendon/ligament allograft or autograft, in order to enhance or accelerate the healing potential of the suture or graft.

The choice of a carrier material is based on biocompatibility, biodegradability, mechanical properties, cosmetic appearance and interface properties. The particular application of the compositions/cultures of non-culture expanded cells will define the appropriate formulation. In another embodiment the non-culture expanded cells can be mixed with a matrix. Potential matrices for compositions/cultures of non-culture expanded cells may be biodegradable and chemically defined. Further matrices are comprised of pure proteins or extracellular matrix components. Other potential matrices are non-biodegradable and chemically defined. Preferred matrices include collagen-based materials, including sponges, such as Helistat.® (Integra LifeSciences, Plainsboro, N.J.), or collagen in an injectable form, as well as sequestering agents, which may be biodegradable, for example, hyalouronic acid-derived. Biodegradable materials, such as cellulose films, or surgical meshes, may also serve as matrices. Such materials could be sutured into an injury site, or wrapped around the tendon/ligament. Another preferred class of carriers are polymeric matrices, where the cell of the invention can be mixed with polymers of poly lactic acid, poly glycolic acid and copolymers of lactic acid and glycolic acid. These matrices may be in the form of a sponge, or in the form of porous particles, and may also include a sequestering agent. Suitable polymer matrices are described, for example, in WO93/00050.

In another embodiment, there is provided a method of use of an isolated, non-culture expanded mesenchymal stem cell in the preparation of a medicament for stimulating or enhancing tissue repair in a subject, wherein the non-culture expanded mesenchymal stem cell is obtained via the methods described herein. In one embodiment, the mesenchymal stem cells are cultured for short periods of time (less than 24 hours). In another embodiment, the cells are transfected or transduced prior to their administration to the subject. In another embodiment, the method is utilized for repairing damage to connective tissue, or in another embodiment non connective tissue.

In another embodiment, there is provided a method of use of an isolated, non-culture expanded mesenchymal stem cell in the preparation of a medicament for stimulating or enhancing tissue formation in a subject, wherein the non-culture expanded mesenchymal stem cell is obtained via the methods described herein.

The term tissue includes, in one embodiment, a connective tissue and in another embodiment a non-connective tissue.

The term "connective tissue" refers hereinabove to bone, cartilage, ligament, skin, fat, tendon, muscle, meniscus and interval disc tissue of a mammalian tissue and stroma.

In another embodiment, the compositions/cultures of non-culture expanded cells of the invention may comprise, other therapeutically useful agents such as, and without being limited to, cytokines, chemokines, leukemia inhibitory factor (LIF/HILDA/DIA), migration inhibition factor, MP52, growth factors including epidermal growth factor (EGF), fibroblast growth factor (FGF), platelet derived growth factor (PDGF), transforming growth factors (TGF-alpha and TGF-beta), and fibroblast growth factor-4 (FGF-4), parathyroid hormone (PTH), insulin-like growth factors (IGF-I and IGF-II), or combinations thereof. Portions of these agents may also be used in compositions of the present invention. Such a composition may be useful for treating defects of the embryonic joint where tendon, ligaments, and bone form simultaneously at contiguous anatomical locations, and may be useful for regenerating tissue at the site of tendon attachment to bone. It is contemplated that the compositions of the invention may also be used in wound healing, such as skin healing and related tissue repair. The types of wounds include, but are not limited to burns, incisions and ulcers.

In another embodiment at least one other agent can be added such as agent that promotes hematopoiesis, such as, for example a cytokine, which participates in hematopiesis. Some non-limiting examples are: CSF-1, G-CSF, GM-CSF, interleukins, interferons, or combinations thereof.

In another embodiment, an agent that promotes the delivery of systemic proteins such as Factor IX, VIII, Growth hormone etc. may be provided to the subject following the incorporation of engrafted mesenchymal stem cells into bone marrow following transplantation.

As used herein, the term "inducing formation" refers to a use in tissue renewal or regeneration so as to ameliorate conditions of tissue, degeneration, depletion or damage such as might be caused by aging, genetic or infectious disease, accident or any other cause, in humans, livestock, domestic animals or any other animal species. In another embodiment the tissue formation is required for tissue development in livestock, domestic animals or any other animal species in order to achieve increased growth for commercial or any other purpose. In another embodiment the tissue formation is required in plastic surgeries, such as, and without being limited to, facial reconstruction in order to obtain a stabilized shape.

As used herein, the term "enhancing tissue repair" or "repairing"refers to healing and/or regeneration of tissue injuries, tears, deformities or defects, and prophylactic use in preventing tissue damage.

In another embodiment, the invention provides a method of use of an isolated, non-culture expanded mesenchymal stem cell in the preparation of a medicament for treating and preventing osteoporosis, which results from a decrease in estrogen, which may be caused by menopause or ovariectomy in women. Use of isolated, non-culture expanded mesenchymal stem cell in the preparation of a medicament for prevention of accelerated bone resorption and inhibition of a decrease of bone volume, bone quality and bone strength is also provided by the invention. In accordance with the methods of the invention, a pharmaceutical composition containing an extract from inflamed tissue as an effective component may be used to maintain or increase bone volume, bone quality, and bone strength. Trabecular connectivity and trabecular unconnectivity may be maintained at healthy levels with the pharmaceutical compositions of the present invention. Osteoporosis and its symptoms such as decreased bone volume, bone quality, and bone strength, decreased trabecular connectivity, and increased trabecular unconnectivity may be treated or prevented by administration of a pharmaceutically effective amount of the extract to a patient in need thereof.

Thus, there is provided a method for maintaining or increasing bone volume, bone quality, or bone strength in a subject, comprising the use of an isolated, non-culture expanded mesenchymal stem cell in the preparation of a medicament for maintaining or increasing bone volume, bone quality, or bone strength in a subject, wherein the non-culture expanded mesenchymal stem cell is obtained via the methods described herein.

It is to be understood that the production of any composition or medicament that utilizes non-culture expanded mesenchymal stem cells, is to be considered as part of this invention.

The compositions/medicaments/cultures of this invention may be utilized in the following applications: (1) for regenerating mesenchymal tissues which have been damaged through acute injury, abnormal genetic expression or acquired disease; (2) repairing damaged mesenchymal tissue by removal of small aliquots of bone marrow, isolation of their mesenchymal stem cells and treatment of damaged tissue with non cultured MSCs combined with a biocompatible carrier suitable for delivering MSCs to the damaged tissues site(s); (3) for producing various mesenchymal tissues; (4) for detecting and evaluating growth factors relevant to MSC self-regeneration and differentiation into committed mesenchymal lineages; (5) for detecting and evaluating inhibitory factors which modulate MSC commitment and differentiation into specific mesenchymal lineages; (6) for developing mesenchymal cell lineages and assaying for factors associated with mesenchymal tissue development. MSCs have pivotal role in the bone marrow environment and have the ability to support hematopoiesis as indicated by many crucial cytokines and growth factors that they constitutively express and secrete (Majumdar et al., 2000); (7) for stimulation of skeletal development in livestock, domestic animals or any other animal species in order to achieve increased growth for commercial or any other purpose; and (8) for treatment of neoplasia or hyperplasia of bone or cartilage or any other tissue, in humans, livestock, domestic animals or any other animal species For these reasons, it's obvious that MSCs are very important for hematopoietic reconstitution. The non-cultured MSCs can be used in combination with hematopoietic transplants.

In another embodiment, the cells can be genetically engineered to express a protein of interest prior to the application to the subject in need. The protein of interest is any macromolecule, which is necessary for cell growth, morphogenesis, differentiation, tissue building or combinations thereof. These are, for example, a bone morphogenic protein, a bone morphogenic-like protein, an epidermal growth factor, a fibroblast growth factor, a platelet derived growth factor, an insulin like growth factor, a transforming growth factor, a vascular endothelial growth factor, cytokines related to hematopoiesis, factors for systemic delivery as such as GH, factor VIII, factor IX or combinations thereof.

The term "cells engineered to express a protein of interest" is defined hereinabove as a cell or to a tissue which had been modified via molecular biologic techniques, for example via recombinant DNA technology, to express any macromolecule which is necessary for cell growth, morphogenesis, differentiation, tissue building or combinations thereof. In another embodiment, cells are thus modified in order to produce an increased amount of any macromolecule, which is necessary for cell growth, morphogenesis, differentiation, tissue building or combinations thereof. The term "increased amount" refers hereinabove to at least 10 times more than an amount normally produced.

The step of 'genetically engineered a cell to express a protein of interest' is performed by the transfection or transduction of the cell with a nucleic acid encoding the protein of interest.

The term "transfection" or "transfected cells" refer to cells in which DNA is integrated into the genome by a method of transfection, i.e. by the use of plasmids or liposomes.

The term "transduction" or "transduced cells" refers to viral DNA transfer for example, by phage or retroviruses. The nucleic acid, which encodes the protein of interest, can be introduced by a vector molecule, as well, and represents an additional embodiment of this invention.

The vector molecule can be any molecule capable of being delivered and maintained, within the target cell, or tissue such that the gene encoding the product of interest can be stably expressed. In one embodiment, the vector utilized in the present invention is a viral or retroviral vector or a non-viral DNA plasmid. According to one aspect, the method includes introducing the gene encoding the product into the cell of the mammalian tissue for a therapeutic or prophylactic use. The viral vectors, used in the methods of the present invention, can be selected from the group consisting of (a) a retroviral vector, such as MFG or pLJ; (b) an adeno-associated virus; (c) an adenovirus; and (d) a herpes virus, including but not limited to herpes simplex 1 or herpes simples 2 or (e) lentivirus. Alternatively, a non-viral vector, such as a DNA plasmid vector, can be used. Any DNA plasmid vector known to one of ordinary skill in the art capable of stable maintenance, within the targeted cell, or tissue upon delivery, regardless of the method of delivery utilized is within the scope of the present invention. Non-viral means for introducing the gene encoding for the product into the target cell are also within the scope of the present invention. Such non-viral means can be selected from the group consisting of (a) at least one liposome, (b) $Ca_3(PO_4)_2$, (c) electroporation, (d) DEAE-dextran, and (e) injection of naked DNA.

The term "nucleic acid" refers to polynucleotides or to ologonucleotides such as deoxyribonucleic acid (DNA), and, where appropriate, ribonucleic acid (RNA) or mimetics thereof. The term should also be understood to include, as equivalents, analogs of either RNA or DNA made from nucleotide analogs, and, as applicable to the embodiment being described, single (sense or antisense) and double-stranded polynucleotides. This term includes oligonucleotides composed of naturally occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, enhanced cellular uptake, enhanced affinity for nucleic acid target and increased stability in the presence of nucleases.

The dosage of the treatment, which is the amount of the cells that are administered in order to obtain a therapeutic effect, is affected by various factors which modify the action of the non-cultured cells' composition, e.g., amount of tendon or ligament tissue desired to be formed, the site of tendon or ligament damage, the condition of the damaged tendon or ligament, the size of a wound, type of damaged tissue, the patient's age, sex, and diet, the severity of any infection, time of administration and other clinical factors. The dosage may vary with the type of matrix used in the reconstitution and the types of additional proteins in the composition. The addition of other known growth factors, such as IGF-I (insulin like growth factor I), to the final composition, may also affect the dosage. Progress can be monitored by periodic assessment of tendon/ligament-like tissue formation, or tendon or ligament growth and/or repair. The progress can be monitored by methods known in the art, for example, X-rays (CT), ultra-sound, MRI, arthroscopy and histomorphometric determinations.

In another embodiment, this invention provides non-culture expanded human adult mesenchymal stem cells. The cells are isolated via the methods disclosed herein, and may be utilized in any of the above-mentioned applications.

In one embodiment, the mesenchymal stem cells will express CD105, CD29 and/or CD44 cell surface antigens. In another embodiment, at least 50%, or in another embodiment, at least 55%, or, in another embodiment, at least 60%, or, in another embodiment, at least 65%, or, in another embodiment, at least 70%, or, in another embodiment, at least 75%, or, in another embodiment, at least 80%, or, in another embodiment, at least 85%, or, in another embodiment, at least 90%, or, in another embodiment, at least 95%, or, in another embodiment, from about 95-100%, of the mesenchymal stem cells expressing CD105, will express CD29 and/or CD44 cell surface antigens.

In another embodiment, less than 25% of the mesenchymal stem cells expressing CD105 will express CD45, CD14, CD34 and/or CD31 cell surface antigens. In another embodiment, less than 20%, or, in another embodiment, less than 15%, or, in another embodiment, less than 10%, or, in another embodiment, less than 7%, or, in another embodiment, less than 5%, or, in another embodiment, between 0 and 5% of the mesenchymal stem cells expressing CD105, will express CD45, CD14, CD34 and/or CD31 cell surface antigens.

It is to be understood that the mesenchymal stem cells are capable of further differentiation to cells of mesenchymal tissue lineage. As discussed hereinabove, the mesenchymal tissue lineage may comprise bone, cartilage, fat, tendon, ligament, muscle or marrow stroma.

In another embodiment, the cells of the invention may be engineered to express at least one protein of interest, where, the protein of interest may comprise a macromolecule necessary for cell growth, morphogenesis, differentiation, tissue building or combinations thereof, each representing a separate embodiment of the invention.

In another embodiment, the macromolecule necessary for cell growth, morphogenesis, differentiation, and/or tissue building is a bone morphogenic protein, a bone morphogenic-like protein, a cytokine, a chemokine, a hormone, an epidermal growth factor, a fibroblast growth factor, a platelet derived growth factor, an insulin like growth factor, a transforming growth factor, a vascular endothelial growth factor, Ang-1, PlGF or combinations thereof.

EXAMPLES

Experimental Procedures

Isolation of hMSCs-enriched Cell Populations:
1) Immunomagnetic Isolation of BM-CD105+ Cells:

Human Bone Marrow (BM) was recovered from heparinized trabecular bone samples obtained from patients undergoing corrective orthopaedic surgery (approved by the Helsinki Committee Board of the Hadassah Medical Center, Jerusalem, Israel). The BM-containing trabecular bone sample was flushed with PBS (Biological Industries, Kibbutz Beit Haemek, Israel). To isolate mono-nuclear cells, whole BM was layered over lymphocyte separation medium (LSM, ICN-Cappel Inc., Aurora, Ohio, USA), and centrifuged at 900 g for 30 minutes, room temperature, without a break.

Mononuclear cells were washed once with PBS and twice with magnetic-activated cell sorting (MACS) buffer (PBS with 0.5% BSA, 2 mM EDTA, PH7.2), counted, and resuspended in MACS buffer at a concentration of $10^7$ cells per 80 ul, transferred to 1.5 ml test tube, to which directly conjugated mouse anti-human CD105 antibody-microbeads (Miltenyi Biotec, Germany) were added and placed on rotator for 45-50 min at 4° C. in the dark. The cells were washed with PBS, resuspended in MACS buffer and separated on a magnetic column MS+ according to the manufacturer's recommendation. Cells that passed through the column were considered CD105− cells. To recover the CD105+ cells, the column was removed from the magnet and the cells were flushed out with MACS buffer. The CD105−, and CD105+ cells were then recovered by centrifugation for future use.

2) BM-hMSCs Enrichment:

Human BM cell aliquots, flushed from trabecular bone samples with complete growth medium, were mixed with RosetteSep™ Mesenchymal Enrichment Cocktail (StemCell Technologies, BC, Canada) at 50 ul cocktail/1 ml BM, and incubated at room temperature for 20 minutes. The BM-enrichment cocktail mixture was then diluted with 2 volumes of PBS containing 2% FCS and 1 mM EDTA, layered over LSM and centrifuged at 900 g for 30 minutes, room temperature, without brake.

Mononuclear cells collected from the interface were considered as mesenchymal stem cells-enriched populations, and were washed with PBS and counted for further use.

Cell Culture:

Either CD105+ or MSCs-enriched populations were resuspended with DMEM supplemented with 2 mM L-glutamine, 100 units/ml penicillin, 100 units/ml streptomycin, and 10% FCS (Biological Industries, Kibbutz Beit Haemek, Israel) and plated in tissue culture dishes at a density of 10,000-15,000 cells/cm$^2$ growth area, at 37° C. in 5% $CO_2$ in air. Medium was changed after 72 h and then after 3-4 days. At day 14-16, cells were detached by incubation with 0.25% trypsin-EDTA for 5-10 min. The cells were then re-plated at a density of 5000-6000 cells/cm$^2$ for expansion. The cells were subcultured as mentioned when reached 90% confluency, and were used for assays or stored in 85% complete medium (DMEM+ 10% FCS), 5% BSA and 10% DMSO (Sigma, St. Louis, Mo., USA) in liquid nitrogen for future use.

Flow Cytometry

Aliquots (0.5–1.5×10$^6$ cells) of fresh human bone marrow mononuclear cells or culture-expanded hMSCs were used for the analysis of cell surface molecules. Cells were washed with PBS, resuspended with FACS buffer consisting of 2% BSA and 0.1% sodium azide (Sigma, St. Louis, Mo., USA) in PBS, and stained with the fluorochrome-conjugated mouse anti-human CD105 (Serotec), CD44, CD29, CD14, CD34, CD45 monoclonal antibodies (DAKO) according to the manufacturer's recommendation, using the mouse monoclonal isotype antibodies (IgG1, IgG2) to determine non-specific fluorescence. Cells were then washed with PBS and resuspended with 0.5 ml FACS buffer and analysed for the expression of the human indicated antigens by FACscan (Becton-Deckinson), and the Cell-Quest software for data collection and analysis.

In-vitro Differentiation Assays.

In order to induce the osteogenic differentiation of hMSCs in vitro, bone marrow derived hMSCs isolated either by the CD105 microbeads or the RosetteSep™ enrichment cocktail were plated at a density of 3000 cells/cm$^2$ in DMEM+10% FCS containing osteogenic supplement consisting of: 0.05 mM ascorbic acid-2-phosphate, 10 mM beta-glycerophosphate, and 0.1 µM dexamethasone (Sigma, St. Louis, Mo., USA). Cells grown with DMEM+10% FCS without osteogenic supplement were used as the negative control. At 1, 2, and 3 weeks after addition of supplement, cells were lysed with alkaline buffer solution (Sigma, St. Louis, Mo., USA), containing 0.5% Triton X100, and 10 mM MgCl2 (for alkaline phosphatase, ALP assay), or 0.5 N HCl solution (for calcium deposition assay). For ALP assay, lysates were incubated with assay buffer containing 0.75 M 2-amino-2-methyl-1-propranolol pH 10.3 for 10 min at 37 C with p-nitrophenylphosphate as a substrate. For calcium depositions assay, cell lysates were incubated at 4 C, for 24 hrs with gentle shaking. Samples were then assayed for calcium content using the Calcium kit (Sigma, St. Louis, Mo., USA). Protein content was mesaured using the BCA protein assay kit (Pierce, Rockford, Ill.).

BM-hMSCs Transplantation at an Ectopic Site:

BM-hMSCs isolated via either CD105 microbeads or RosetteSep™cocktail were immediately labeled with Vybrant DiI cell-labeling solution (Molecular Probes). Labeling was performed by re-suspending cells in serum-free DMEM at a concentration of $1 \times 10^6$ cells/ml, mixed with 15 µl per ml Vybrant DiI solution, and incubated for 30 minutes at 37° C. and 5% $CO_2$ on shaker, in the dark. DiI-labeled non-cultured cells ($1-1.5 \times 10^6$/implant) were mixed with 5 µg recombinant human BMP-2 (rhBMP2), mounted on a collagen sponge (Duragen) and transplanted subcutaneously into 6-8 week old NOD/SCID mice. Implants were harvested 2 and 4 weeks post-transplantation.

Transplantations into Skull Defects:

For the skull-defect assay, we used male CD-1 nude mice. The mice were anesthetized with ketamine-xylazine mixture, the scalp was dissected to the skull and a 5-mm-diameter full-thickness circular skull defect. This defect, a nonhealing critical-sized defect (Krebsbach et al., 1998), was created at the apex of the skull with use of a dental burr, with minimal penetration of the dura. The mice were divided into three groups, and a collagen sponge (Duragen) cut to form-fit the defect was used as a matrix. The scalp was closed with use of nylon suture. At 3 weeks, mice were sacrificed and the skull specimens were dissected free from the soft tissue and fixed in 4% formalin, decalcified by decal rapid solution, paraffin embedded, and 5-7 micron sections were prepared and stained by H&E for the evaluation of new bone formation.

Experimental Results

Example 1

Figure 1C:
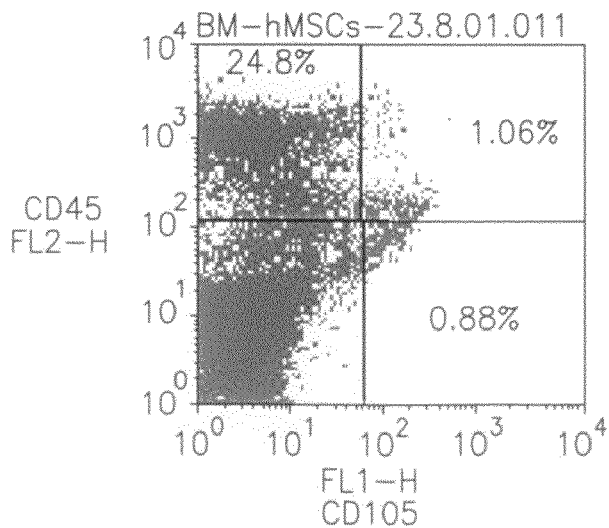
Figure 1D:
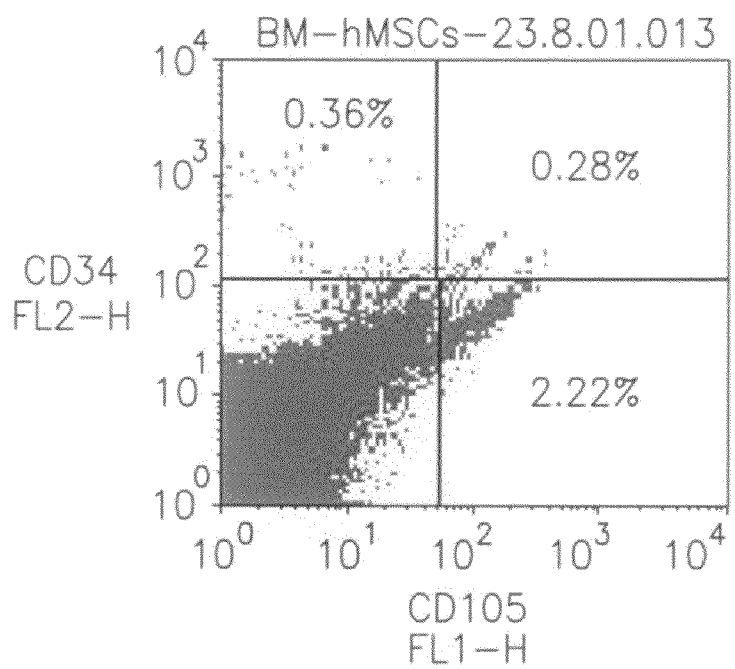
Figure 1E:
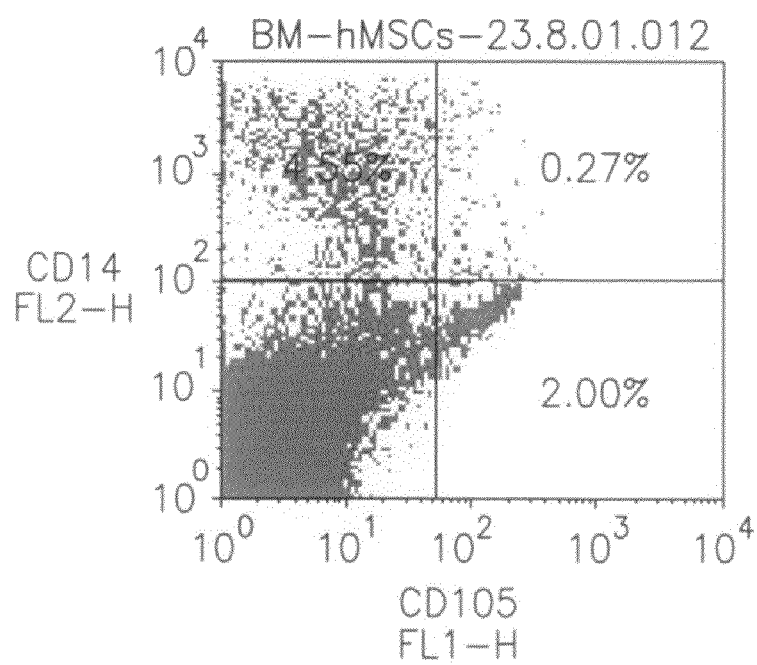

Isolation of hMSCs and Flow Cytometry:

In order to characterize the CD105+ cell population in human bone marrow (BM), human BM-derived mononuclear cells were analyzed for co-expression of CD105 antigen and other hematopoietic markers. Marker FACS analysis of freshly separated human BM mononuclear cells demonstrated that CD105 was co-expressed with other hematopoietic markers at low levels, except for CD45, which was co-expressed at higher percentages on CD105 cells (about 40%, FIG. 1C). More importantly, however, was the minimal expression of CD14 (a monocyte marker) on CD105+ cells, indicating that macrophages, the hematopoietic cell population from bone marrow with the greatest adherence to plastic, did not comprise the CD105+ cell population isolated (FIG. 1E).

Figure 2A:
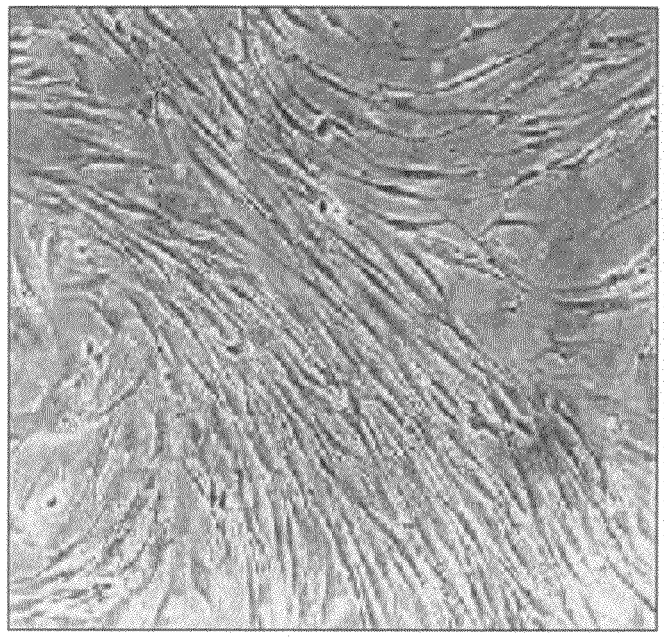
FIG. 2 shows in vitro differentiation of expanded hMSCs isolated with CD105 microbeads to osteogenic lineage. A: Alkaline phosphatase activity in cell lysates was assayed at 1, 2, and 3 weeks after the addition of osteogenic supplement. Activity was assessed as the release of p-nitrophenyl per minute normalized to total cell protein (in micrograms). B: Calcium deposition measured in cell lysates, assessed as the formation of Calcium-Cresolphthalein Complexon complex, and expressed as optical density (OD) at 575 nm, which is directly proportional to the calcium concentration in the sample. Note significant increase (*$P<0.05$) in the cells cultured with osteogenic supplement (+Suppl.) compared to the cells cultured without osteogenic supplement (−Suppl.). The bars represent the mean (±SEM) ALP (A), or calcium deposition (B), from three individual wells.
Figure 2B:
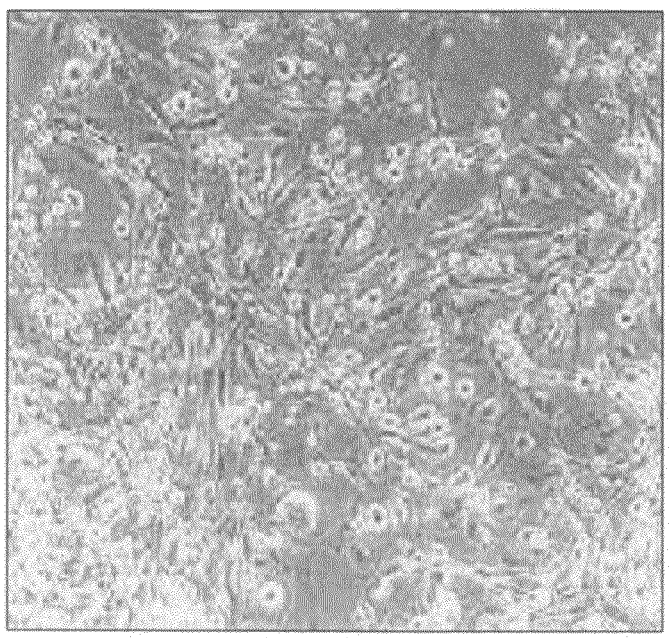
Figure 2C:
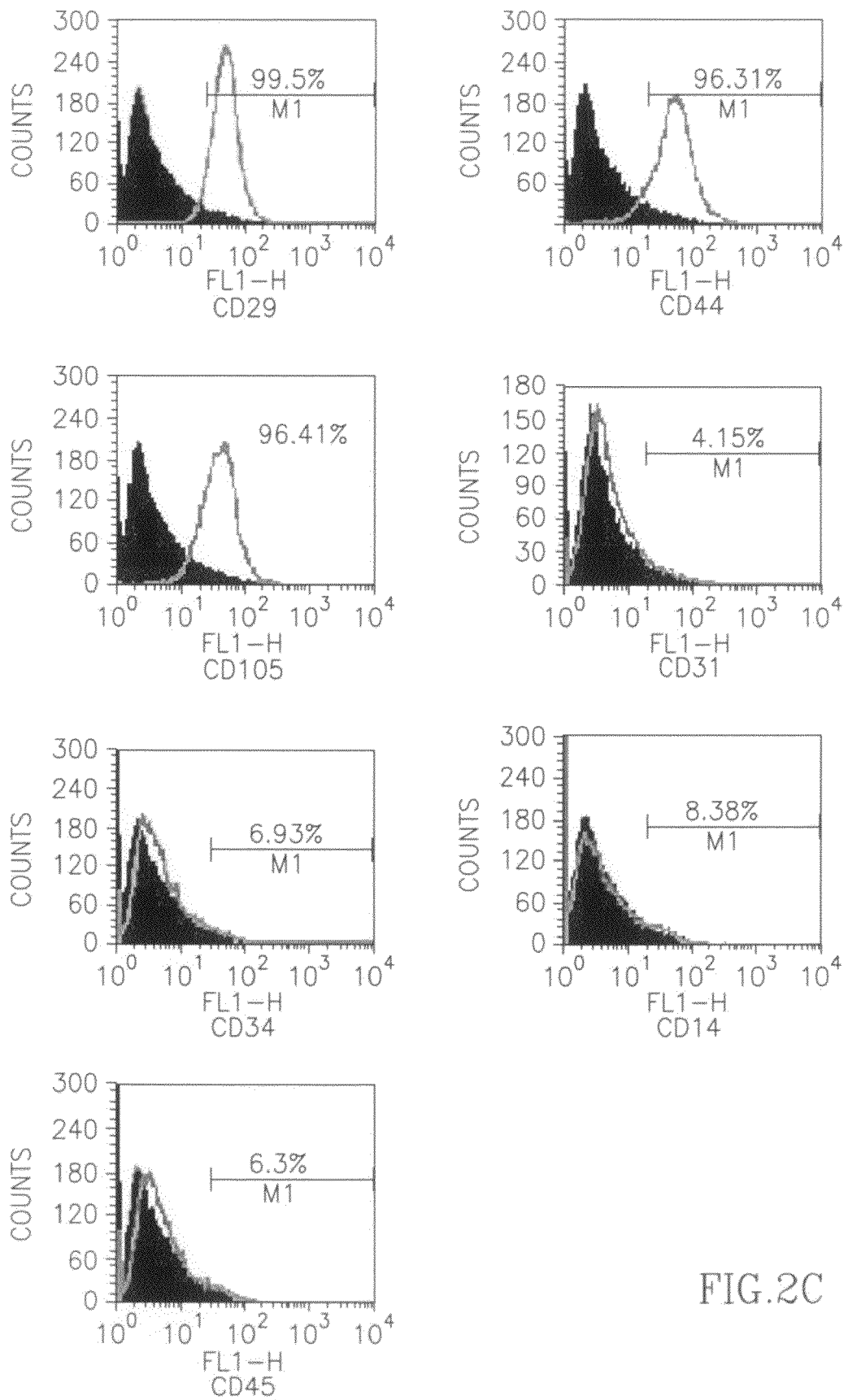

CD105+ cells were isolated from human BM mononuclear cells via CD105-microbeads, then plated for expansion. Colonies of fibroblastic-like cells appeared within 7-10 days following initial plating, and were a morphologically homogenous population, whereas whole BM mononuclear cells (without separation via CD105 microbeads) were a mixed population of cells, consisting of fibroblast- and macrophage-like cells (FIGS. 2A and 2B). Marker FACS analysis of the culture-expanded hMSCs (passages 3-6) isolated by this method demonstrated cells positive for CD105, CD29 and CD44 and negative for CD14 and CD45 (FIG. 2C).

Example 2

Figure 3A:
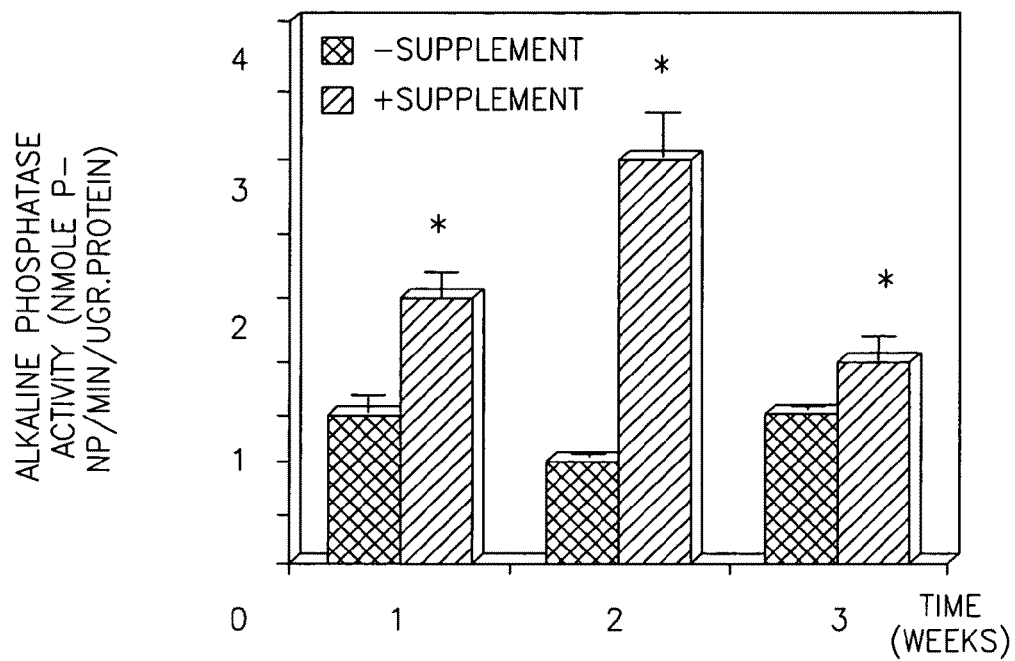
FIG. 3 demonstrates morphology and flow cytometry analysis of culture-expanded CD105+ cells. The cells were isolated from bone marrow using microbeads coupled-antibody against CD105, plated in media and maintained in culture as indicated. Photomicrograph of 10-day cultured CD105+ cells (A, X 40), and whole BM-MNCs (B, X 40). C: Expression of surface molecules on culture expanded (passage 3-5) CD105+ cells.
Figure 3B:
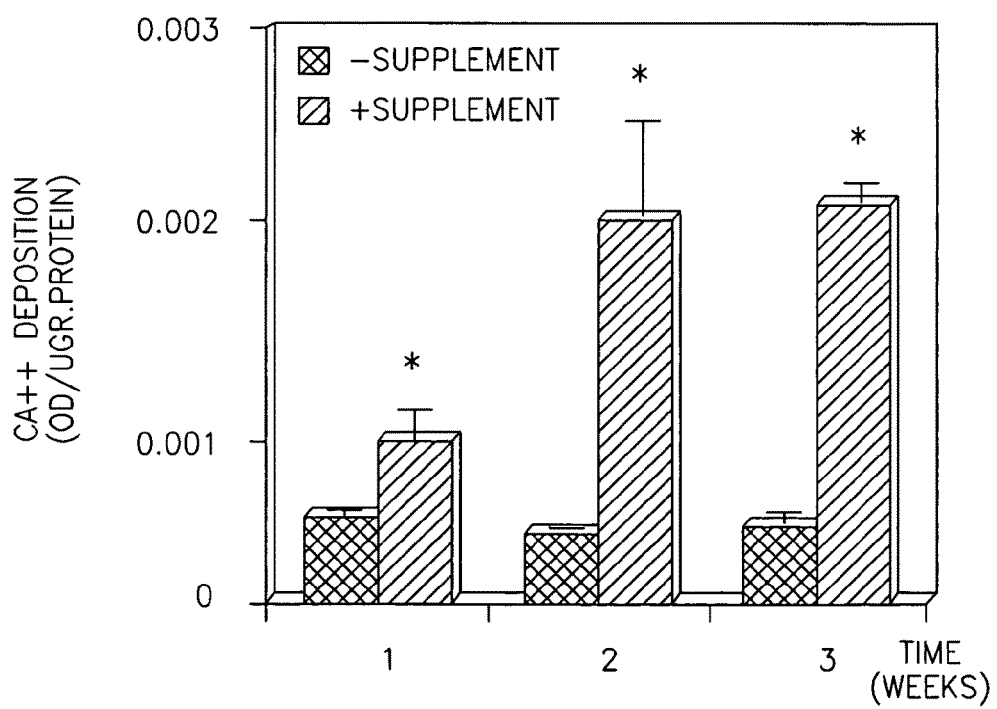
Figure 4C:
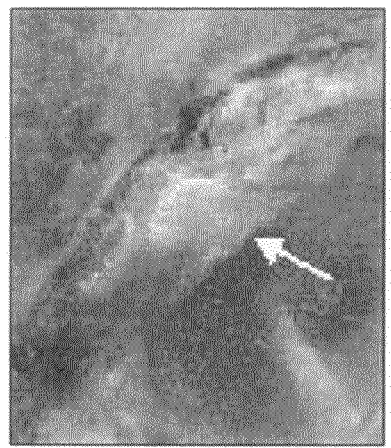
FIG. 4 demonstrates the in vivo osteogenic potential of fresh BM-derived CD105+ cells. A 5-mm-diameter circular defect was created in the radius of 6-8-week-old male CD-1 nude mice. Non-cultured, fresh BM-derived CD105+cells (isolated by the CD105 microbeads) were mounted on collagen sponges and transplanted in the defect site. Twenty days post transplantation, mice were sacrificed, calvariae dissected from other soft tissues, analyzed by x-ray, and histologic analysis for evidence of new bone formation. A, B: X-rays of the calvariae specimens transplanted with BM-CD105+ (A), and BM-CD105− cells (B), note radio-opaque region in the defect transplanted with BM-CD105+ cells (A, doubled arrows). C, D, E, F: Micrograph of calvariae specimens transplanted with BM-CD105+ cells (C, D), and BM-CD105− cells (E, F). Note newly formed bone on the margins of the defect in specimen transplanted with BM-CD105+cells (arrows).
Figure 4B:
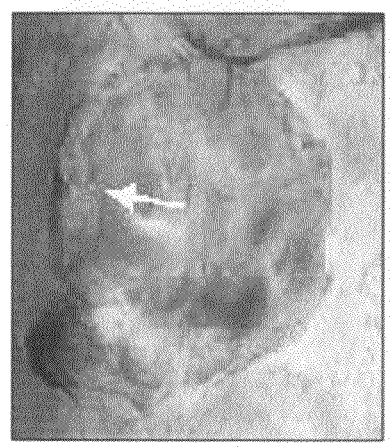
Figure 4A:
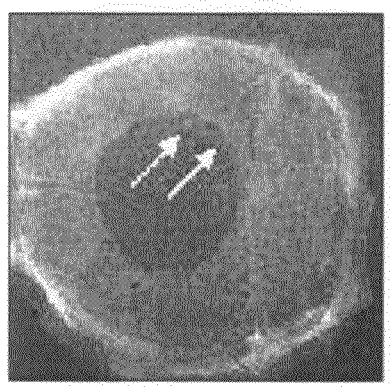
Figure 4F:
Figure 4E:
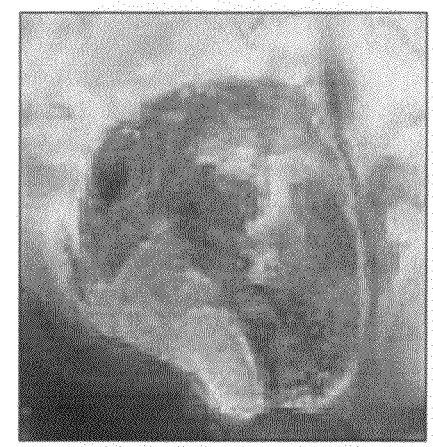
Figure 4D:
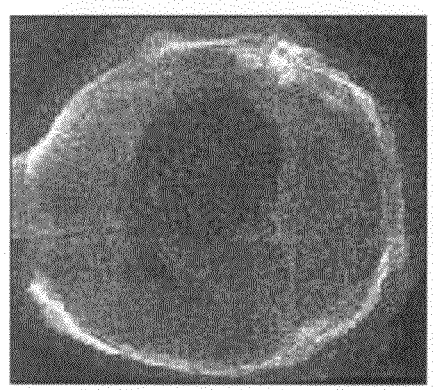

In vitro Osteogenic Differentiation:

In order to determine the in vitro osteogenic potential of CD105+cells, CD105+ cells were cultured following expansion (passages 3-5) under conditions inducing differentiation of mesenchymal stem cells to cells of osteogenic lineage (Pittenger et al., 1999). Significant increase in alkaline phosphatase activity was evident in induced hMSCs (with supplement), as compared to non-induced hMSCs (without supplement), during the 3 weeks of differentiation (FIG. 3A). Continual, significant increase in calcium deposition (expressed as OD at 575 nm) was observed during the differentiation period (1, 2, and 3 weeks, FIG. 3B).

Example 3

Non-culture Expanded, CD105+ hMSCs Form Cartilage and Bone in vivo:

Freshly isolated, non-culture expanded hMSCs isolated via CD105 microbead separation were transplanted into skull-defects induced in CD-1 nude mice, in order to determine their in vivo osteogenic potential. New bone formation was observed in sections processed and stained with H&E, whereas no evidence of newly formed bone was observed in similarly injured mice transplanted with collagen inserts containing CD105− cells (FIG. 4) or collagen inserts alone (data not shown).

Osteogenic differentiation of non-culture expanded hMSCs in vivo was also demonstrated via implanting the cells into NOD/SCID mice. Non-culture expanded hMSCs ($1-1.5 \times 10^6$ cells) labeled with DiI were mixed with rhBMP2, loaded onto collagen sponges (Duragen) serving as scaffolding and transplanted under the skin of NOD/SCID mice. Cartilage and bone formation was detected in harvested implants, two weeks post-transplantation (FIGS. 5A and B). Non-culture expanded hMSCs were identified by confocal microscopy in newly formed cartilage and bone tissue. DiI-labeled chondrocytes (FIG. 5C) and osteoblasts (FIG. 5D) were detected within the implant.

REFERENCES

Caplan A I, Bruder S P. Mesenchymal stem cells. Building blocks for molecular medicine in the 21st century. Trends Mol Med 2001 June; 7(6):259-64

Friedenstein Aia Stromal bone marrow cells and the hematopoietic microenvironment *Arkh. Patol.* 1982, 44, 10.

Gronthos S., Simmons P J. The growth factor requirements of STRO-1-positive human bone marrow stromal precursors under serum-deprived conditions in vitro *Blood* 1995, 85, 4.

Haynesworth, S E.; Goshima, J.; Goldberg, V M. Characterization of cells with osteogenic potential from human marrow; Caplan, A I. *Bone* 1992, 13, 1.

Horwitz E M, Prockop D J, Fitzpatrick L A, Koo W W, Gordon P L, Neel M, Sussman M, Orchard P, Marx J C, Pyeritz R E, Brenner M K. Transplantability and therapeutic effects of bone marrow-derived mesenchymal cells in children with osteogenesis imperfecta: Nat Med 1999 March; 5(3):309-13

Kadiyala S, Young R G, Thiede M A, Bruder S P. Culture expanded canine mesenchymal stem cells possess osteochondrogenic potential in vivo and in vitro. Cell Transplant 1997 March-April; 6(2):125-34

Krebsbach P H, Mankani M H, Satomura K, Kuznetsov S A, Robey P G. Repair of craniotomy defects using bone marrow stromal cells: Transplantation 1998 Nov. 27; 66(10):1272-8

Lee K, Majumdar M K, Buyaner D, Hendricks J K, Pittenger M F, Mosca J D. Human mesenchymal stem cells maintain transgene expression during expansion and differentiation: Mol Ther 2001 June; 3(6):857-66

Liechty, K W.; MacKenzie, T C.; Shaaban, A F.; Radu, A.; Moseley, A M.; Deans, R.; Marshak, D R.; Flake, A W. Human mesenchymal stem cells engraft and demonstrate site-specific differentiation after in utero transplantation in sheep. *Nat. Med.* 2000, 6, 11.

Mackay A M, Beck S C, Murphy J M, Barry F P, Chichester C O, Pittenger M F: Chondrogenic differentiation of cultured human mesenchymal stem cells from marrow. Tissue Eng 1998 Winter; 4(4):415-28

Majumdar M K, Banks V, Peluso D P, Morris E A. Isolation, characterization, and chondrogenic potential of human bone marrow-derived multipotential stromal cells: J Cell Physiol 2000 October; 185(1):98-106

Majumdar M K, Thiede M A, Haynesworth S E, Bruder S P, Gerson S L: Human marrow-derived mesenchymal stem cells (MSCs) express hematopoietic cytokines and support long-term hematopoiesis when differentiated toward stromal and osteogenic lineages. J Hematother Stem Cell Res 2000 December; 9(6):841-8

Pittenger M F, Mackay, A M, Beck, S C. Human mesenchymal stem cells: progenitor cells for cartilage, bone, fat and stroma. Mol. Biol. Cell. 1996 7:305a.

Pittenger M F, Mackay A M, Beck S C, Jaiswal R K, Douglas R, Mosca J D, Moorman M A, Simonetti D W, Craig S, Marshak D R. Multilineage potential of adult human mesenchymal stem cells Science 1999 Apr. 2; 284(5411):143-7

Turgeman G, Pittman D D, Muller R, Kurkalli B G, Zhou S, Pelled G, Peyser A, Zilberman Y, Moutsatsos I K, Gazit D. Engineered human mesenchymal stem cells: a novel platform for skeletal cell mediated gene therapy: J Gene Med 2001 May-June; 3(3):240-51

Toma C, Pittenger M F, Cahill K S, Byrne B J, Kessler P D. Human mesenchymal stem cells differentiate to a cardiomyocyte phenotype in the adult murine heart. Circulation 2002 Jan. 1; 105(1):93-8

Yoo J U, Barthel T S, Nishimura K, Solchaga L, Caplan A I, Goldberg V M, Johnstone B.: J Bone Joint Surg Am 1998 December; 80(12):1745-57

Young R G, Butler D L, Weber W, Caplan A I, Gordon S L, Fink D J. J Orthop Res 1998 July; 16(4):406-13.

What is claimed is:

1. A method of generating a mesenchymal tissue in a human subject in need thereof, the method comprising administering to the subject non-culture expanded mesenchymal stem cells obtained by:
   (i) contacting a non-culture expanded human cell population with an antibody that binds to a surface molecule expressed on mesenchymal stem cells within said human cell population, so as to form a cell-antibody-complex;
   (ii) recovering said mesenchymal stem cell from said complex;
   (iii) maintaining said recovered mesenchymal stem cells under conditions preventing significant cellular expansion, thereby obtaining the non-culture expanded mesenchymal stem cells,
   thereby generating the mesenchymal tissue in the human subject.

2. The method of claim 1, wherein said non-culture expanded human cell population comprises unfractionated bone marrow, unfractionated human blood, unfractionated human dermis, unfractionated human periosteum, unfractionated muscle or unfractionated human fat.

3. The method of claim 1, wherein the recovered mesenchymal stem cells are capable of further differentiating into differentiated cells of mesenchymal tissue lineage.

4. The method of claim 3, wherein said mesenchymal tissue lineage is bone, cartilage, fat, tendon, ligament, muscle or marrow stroma.

5. The method of claim 3, wherein said mesenchymal tissue lineage is kidney tissue, liver tissue, spleen tissue or neuronal tissue.

6. The method of claim 1, wherein said antibody interacts with at least one human CD 105 antigen.

7. The method of claim 1, wherein said antibody interacts with at least one human CD29 or CD44 antigen.

8. The method of claim 1, wherein said antibody is supported on a column, plastic, array or magnetic bead.

9. The method of claim 1, wherein said mesenchymal stem cells are further genetically engineered to express a protein of interest.

10. The method of claim 9, wherein said protein of interest is a macromolecule necessary for cell growth, morphogenesis, differentiation, or tissue building and combinations thereof.

11. The method of claim 1, wherein the mesenchymal tissue is selected from the group consisting of a cartilage tissue, a bone tissue, a tendon tissue, a ligament tissue, a neuronal tissue, a striated muscle tissue, a cardiac muscle tissue, a spleen tissue, a liver tissue and a kidney tissue.

12. The method of claim 1, wherein the mesenchymal tissue is a bone tissue.

13. The method of claim 1, wherein said mesenchymal stem cells have been cultured 24 hours or less.

14. A method of repairing or inducing formation of a bone in a subject, the method comprising administering a population of non-culture expanded human mesenchymal stem cells enriched for CD105+ mesenchymal stem cells to a bone defect in said subject.

15. The method of claim 14, wherein said mesenchymal stem cells are fresh mesenchymal stem cells.

16. The method of claim 14, wherein said mesenchymal stem cells are cyro-preserved cells.

17. The method of claim 14, wherein said mesenchymal stem cell population is bone marrow derived cells.

18. The method of claim 1, wherein the source of said non-culture expanded human mesenchymal stem cell population is human fat.

19. The method of claim 14, wherein the source of said non-culture expanded human mesenchymal stem cell population is human fat.

20. The method of claim 14, wherein the population of non-culture expanded human mesenchymal stem cells is enriched for CD105+ cells by negative selection of non-mesenchymal cell subpopulations.

21. The method of claim 20, wherein said negative selection is via using antibodies directed to the surface of said non-mesenchymal cell subpopulations.

22. The method of claim 14, wherein said mesenchymal stem cells have been cultured 24 hours or less.

* * * * *